(12) United States Patent
Christel et al.

(10) Patent No.: US 6,368,871 B1
(45) Date of Patent: Apr. 9, 2002

(54) NON-PLANAR MICROSTRUCTURES FOR MANIPULATION OF FLUID SAMPLES

(75) Inventors: Lee Allan Christel, Palo Alto; Gregory T. A. Kovacs, Stanford; William A. McMillan, Cupertino; M. Allen Northrup, Berkeley; Kurt E. Petersen, San Jose; Farzad Pourahmadi, Fremont, all of CA (US)

(73) Assignee: Cepheid, Sunnyvale, CA (US)

( * ) Notice: Subject to any disclaimer, the term of this patent is extended or adjusted under 35 U.S.C. 154(b) by 0 days.

(21) Appl. No.: 08/910,434

(22) Filed: Aug. 13, 1997

(51) Int. Cl.$^7$ ............... G01N 1/10; B01D 37/00; B01D 57/02; B01F 5/06
(52) U.S. Cl. ............ 436/180; 210/767; 204/450; 204/600; 366/336; 422/100; 422/68.1
(58) Field of Search ............ 210/767; 204/450, 204/451, 452, 453, 454, 455, 456, 600, 601, 602, 603, 604, 605; 366/336, 340, 341; 422/68.1, 100, 101; 435/287.2, 288.5

(56) References Cited

U.S. PATENT DOCUMENTS

| | | | |
|---|---|---|---|
| 4,642,220 A | | 2/1987 | Björkman .................... 422/101 |
| 4,891,120 A | * | 1/1990 | Sethi et al. .................. 204/600 |
| 4,895,500 A | | 1/1990 | Hok et al. .................... 417/566 |
| 4,908,112 A | * | 3/1990 | Pace ............................ 204/299 |
| 4,908,318 A | | 3/1990 | Lerner ......................... 435/270 |
| 4,915,812 A | * | 4/1990 | Parce et al. .................. 204/403 |
| 4,921,952 A | | 5/1990 | Longmire et al. ............. 536/27 |
| 4,923,978 A | | 5/1990 | McCormick et al. ......... 536/27 |
| 5,114,858 A | | 5/1992 | Williams et al. ............. 435/270 |
| 5,124,444 A | | 6/1992 | Van Ness et al. ............. 536/27 |
| 5,188,963 A | | 2/1993 | Stapleton .................... 435/299 |
| 5,234,809 A | | 8/1993 | Boom et al. ................... 435/91 |
| 5,296,375 A | | 3/1994 | Kricka et al. ............... 435/291 |
| 5,304,487 A | | 4/1994 | Wilding et al. ............. 435/291 |
| 5,330,916 A | | 7/1994 | Williams et al. ............. 435/311 |

(List continued on next page.)

FOREIGN PATENT DOCUMENTS

| | | | | |
|---|---|---|---|---|
| GB | WO 96/12541 | * | 5/1996 | ......... B01D/11/04 |
| WO | WO 95/12808 | | 5/1995 | |
| WO | WO 9607954 A | * | 3/1996 | |

OTHER PUBLICATIONS

Brody et al., "Deformation and Flow of Red Blood Cells in a Synthetic Lattice: Evidence for an Active Cytoskeleton", *Biophysical Journal* 68:2224–2232 (1995).

(List continued on next page.)

*Primary Examiner*—Jill Warden
*Assistant Examiner*—Monzer R Chorbaji
(74) *Attorney, Agent, or Firm*—Heller Ehrman White & McAuliffe LLP

(57) ABSTRACT

This invention comprises an apparatus and method for the manipulation of materials, including particles, cells, macromolecules, such as proteins, nucleic acids and other moieties, in fluid samples. The apparatus comprises an enclosed chamber on a chip having an internal microstructure with surface area substantially greater than the facial surface area of the internal structure. Generally the internal microstructure comprises a continuous network of channels, each of which has a depth substantially greater than its width. The network may comprise a single channel, a single channel with multiple branches, multiple channels, multiple channels with multiple branches, and any combination thereof. The internal structure may present an inert, non-reactive surface, or be coated with a reactive ligand, or be electrically conductive and optionally be coated with an electrical insulator. Discrete portions of the internal structure may differ in structural and surface properties. Multiple chips may be linked together to create a multiplexed array of chambers, optionally linked to other analytical devices.

22 Claims, 11 Drawing Sheets

U.S. PATENT DOCUMENTS

| | | | |
|---|---|---|---|
| 5,342,931 A | | 8/1994 | Woodard et al. ............ 536/25.4 |
| 5,352,777 A | | 10/1994 | Jhingan ...................... 536/25.4 |
| 5,374,522 A | | 12/1994 | Murphy et al. ................ 435/6 |
| 5,422,241 A | | 6/1995 | Goldrick et al. ............... 435/6 |
| 5,427,663 A | * | 6/1995 | Austin et al. ............ 204/180.1 |
| 5,427,946 A | | 6/1995 | Kricka et al. ............... 435/291 |
| 5,438,129 A | | 8/1995 | Woodard et al. ........... 536/25.4 |
| 5,443,890 A | | 8/1995 | Ö hman .................... 428/167 |
| 5,458,761 A | * | 10/1995 | Kamahori et al. .......... 204/602 |
| 5,500,071 A | * | 3/1996 | Kaltenbach et al. .......... 422/70 |
| 5,534,054 A | | 7/1996 | Woodard et al. ....... 106/287.11 |
| 5,543,305 A | | 8/1996 | Cummins et al. .......... 435/91.1 |
| 5,580,435 A | | 12/1996 | Kovacs ...................... 204/603 |
| 5,587,128 A | | 12/1996 | Wilding et al. ............... 422/50 |
| 5,616,701 A | | 4/1997 | Woodard et al. ........... 536/25.4 |
| 5,641,400 A | * | 6/1997 | Kaltenbach et al. ........ 204/451 |
| 5,705,018 A | * | 1/1998 | Hartley ....................... 156/345 |
| 5,716,852 A | * | 2/1998 | Yager et al. ................ 436/172 |
| 5,741,639 A | * | 4/1998 | Ensing et al. ............... 204/452 |
| 5,842,787 A | * | 12/1998 | Kopf-Sill et al. ........... 366/340 |
| 5,846,727 A | * | 12/1998 | Soper et al. ................ 204/451 |
| 5,858,188 A | * | 1/1999 | Soane et al. ................ 204/450 |
| 5,869,004 A | * | 2/1999 | Parce et al. ................ 422/100 |
| 5,880,071 A | * | 3/1999 | Parce et al. ................ 204/453 |
| 5,921,678 A | * | 7/1999 | Desai et al. ................ 366/336 |
| 5,932,100 A | * | 8/1999 | Yager et al. ................ 210/634 |
| 5,972,710 A | * | 10/1999 | Weigl et al. .................. 436/34 |
| 6,042,709 A | * | 3/2000 | Parce et al. ................. 204/453 |
| 6,068,752 A | * | 5/2000 | Dubrow et al. ............. 204/604 |
| 6,080,295 A | * | 6/2000 | Parce et al. ................. 204/451 |
| 6,090,545 A | * | 7/2000 | Wohlstadter et al. .......... 435/6 |
| 6,153,073 A | * | 11/2000 | Dubrow et al. ............. 204/453 |
| 6,156,273 A | * | 12/2000 | Regnier et al. ............... 422/70 |
| 6,168,948 B1 | * | 1/2001 | Anderson et al. ........ 435/287.2 |

OTHER PUBLICATIONS

Branebjerg et al., "Fast Mixing by Lamination", Proceedings of the Conference on MEMS, Feb. 11–15, 1996, San Diego, CA.

Klaassen et al., "Silicon Fusion Bonding and Deep Reactive Ion Etching: A New Technology for Microstructures", *Sensors and Actuators A* 52:132–139 (1996).

Brody et al., "Diffusion–Based Extraction in a Microfabricated Device", *Sensors and Actuators A* 58:13–18 (1997).

Maluf, N., "Silicon Fusion Bonding Plus DRIE Delivers Design Flexibility", *Micromachine Devices* 2:4–5 (1997).

* cited by examiner

US 6,368,871 B1

NON-PLANAR MICROSTRUCTURES FOR MANIPULATION OF FLUID SAMPLES

FIELD OF THE INVENTION

This invention relates to an apparatus and method for the manipulation of materials, including macromolecule s, such as proteins, nucleic acids and other moieties, in fluid samples.

DESCRIPTION OF RELATED ART

Since Nobelist Richard Feynman first urged scientists and engineers in 1959 to pursue ultra-small technology, numerous devices have been described in the art for the miniaturization and minimalization of analytical systems.

Austin et al. in U.S. Pat. No. 5,427,663 describe a microlithographic array for macromolecule and cell fractionation. This apparatus has channels of a depth commensurate in size to that of the microstructures in the fluid sample, so that the microstructures are restricted to flow in essentially a single layer. The use of traditional etching techniques limits the depth of the channels.

Heller et al in PCT Publication No. WO 95/12808 describe a self addressable self-assembling microelectronic system and device which can actively carry out controlled multi-step and multiplex reactions in microscopic formats. The device has a matrix of addressable microscopic locations on its surface.

Pace, in U.S. Pat. No. 4,908,112, teaches the use of micro-fabrication techniques to produce a capillary gel electrophoresis system on a silicon substrate. Multiple electrodes are incorporated into the system to move molecules through the separation medium within the device.

Branebjerg et al., in "Fast mixing by Lamination", Proceedings of the Conference on MEMS, Feb. 11–15, 1996, San Diego, Calif., disclose a micromachined device for mixing of small flowing fluid volumes.

Klaassen et. al. in Sensors and Actuators A 52:132–139 (1996) disclose developments in the technique of deep reactive ion etching (DRIE), which when combined with silicon fusion bonding (SFB), make it possible to etch nearly the entire range of microstructure thicknesses in single crystal silicon.

The disclosures of the foregoing patents and publications are incorporated herein by reference.

Despite these advances in the art, there remains a need to efficiently extract analyte from large volumes of raw specimen and then to elute the analyte into a very small volume to assure that the final concentration is above the detection limit of the assay method. Prior art devices are generally not compatible with microfluidics nor easily integrated into small analytical systems. None of the prior art methods is efficient nor able to concentrate extracted materials. The present invention overcomes many limitations of the prior art devices for extraction and purification of materials from fluid samples, including biological specimens.

SUMMARY OF THE INVENTION

This invention comprises an apparatus and method for the manipulation of materials, including macromolecules, such as proteins, nucleic acids and other moieties, in fluid samples. The apparatus comprises an enclosed chamber on a chip having an internal microstructure with surface area substantially greater than the facial surface area of the internal structure. The chip may contain integrated heating elements. The internal structure may present an inert, non-reactive surface, or be coated with a reactive ligand, or be electrically conductive and optionally be coated with an electrical insulator. Discrete portions of the internal structure may differ in microstructure and surface properties from other portions.

Generally the internal microstructure comprises a continuous network of channels, each of which has a depth substantially greater than its width. The network may comprise a single channel, a single channel with multiple branches, multiple channels, multiple channels with multiple branches, and any combination thereof.

In one embodiment, the network of channels is so extensive so as to form an internal structure which comprises an array of non-contiguous microcolumns. This embodiment may alternatively be considered as an enclosed, high surface area chamber, having a plurality of independent, non-contiguous columns within said chamber, and at least one port, wherein said columns selectively interact with materials in the sample. In this embodiment, the columns may extend across the smallest dimension of the chamber and may optionally be provided with a coating which selectively retains target moieties, including macromolecules, particularly nucleic acids. Likewise, the columns may be electrically conductive and optionally covered with an electrical insulator.

Also provided is a general method for manipulating charged materials in a fluid sample by contacting the sample with a thin film electronic extractor having an insulator film and an underlying conductor to which a voltage is applied.

BRIEF DESCRIPTION OF THE DRAWINGS

FIG. 1a shows an array of microcolumns with inlet and outlet portals. FIG. 1b is a magnified view of a portion of the round columnar array; FIG. 1c shows an eccentric microcolumnar geometry. In FIG. 1d a single row of eccentric microstructures is pictured at one end of a chamber. FIG. 1e is a micrograph of a channeled chamber showing six converging channels. FIG. 1f shows two converging channels and a series of islands in the merged channel. FIG. 1g shows a multiport multichanneled device FIG. 1h shows a device with three converging channels, one with an inlet port.

DETAILED DESCRIPTION OF THE INVENTION

Figure 1A:
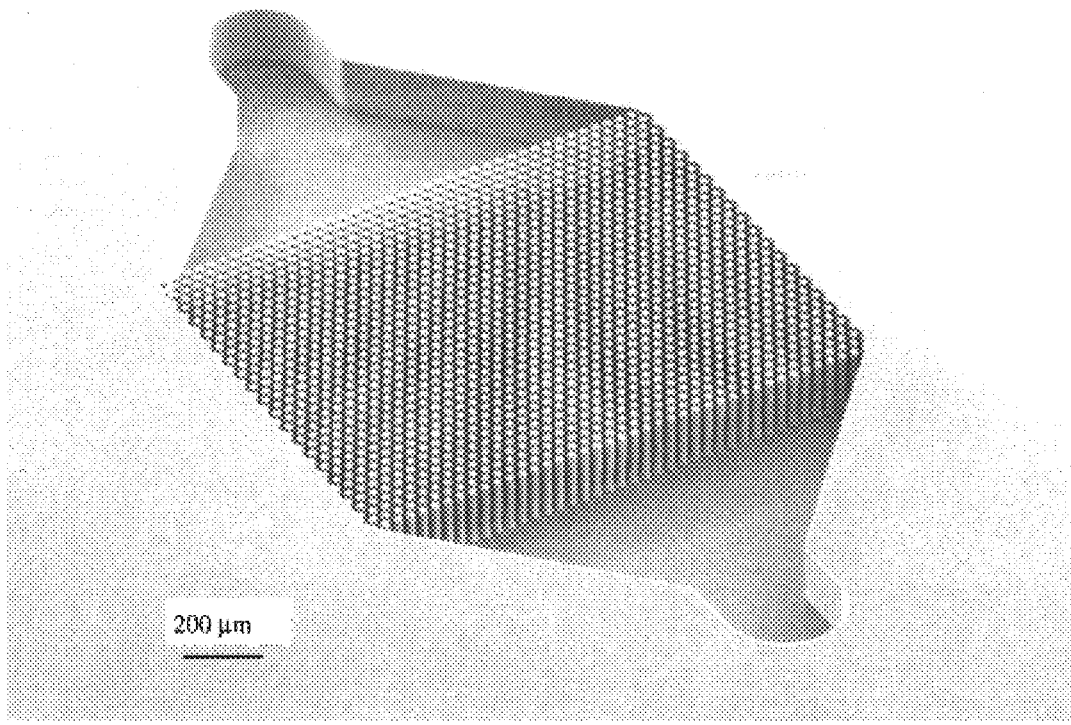
FIGS. 1a–1h are scanning electron micrographs of devices of this invention exemplifying different arrays of microstructures etched in silicon.
Figure 1B:
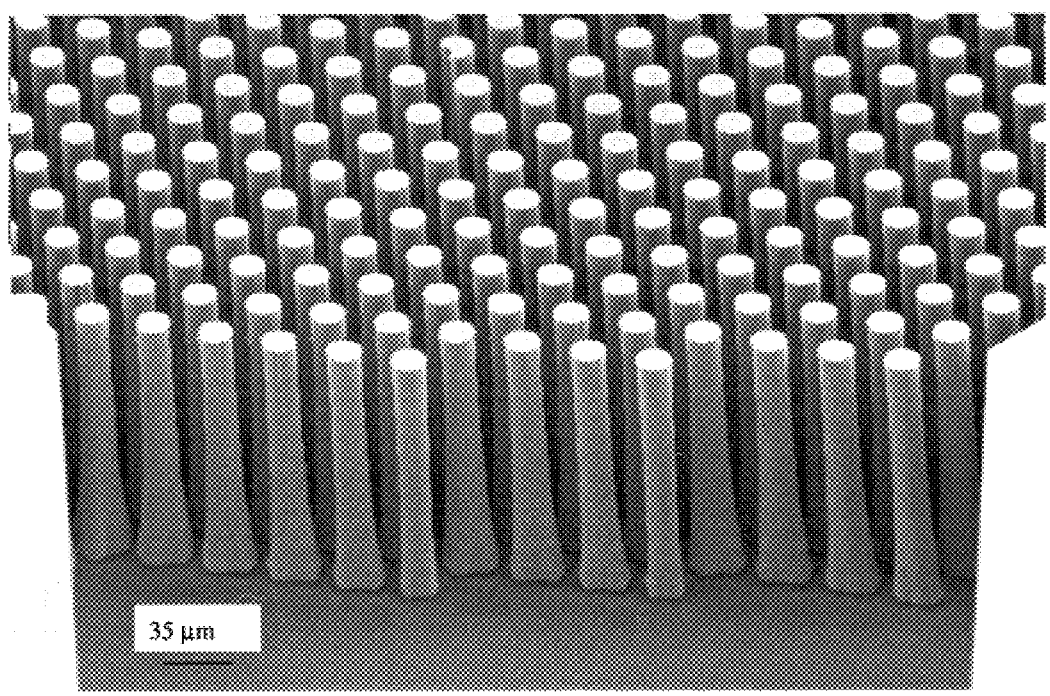
Figure 1C:
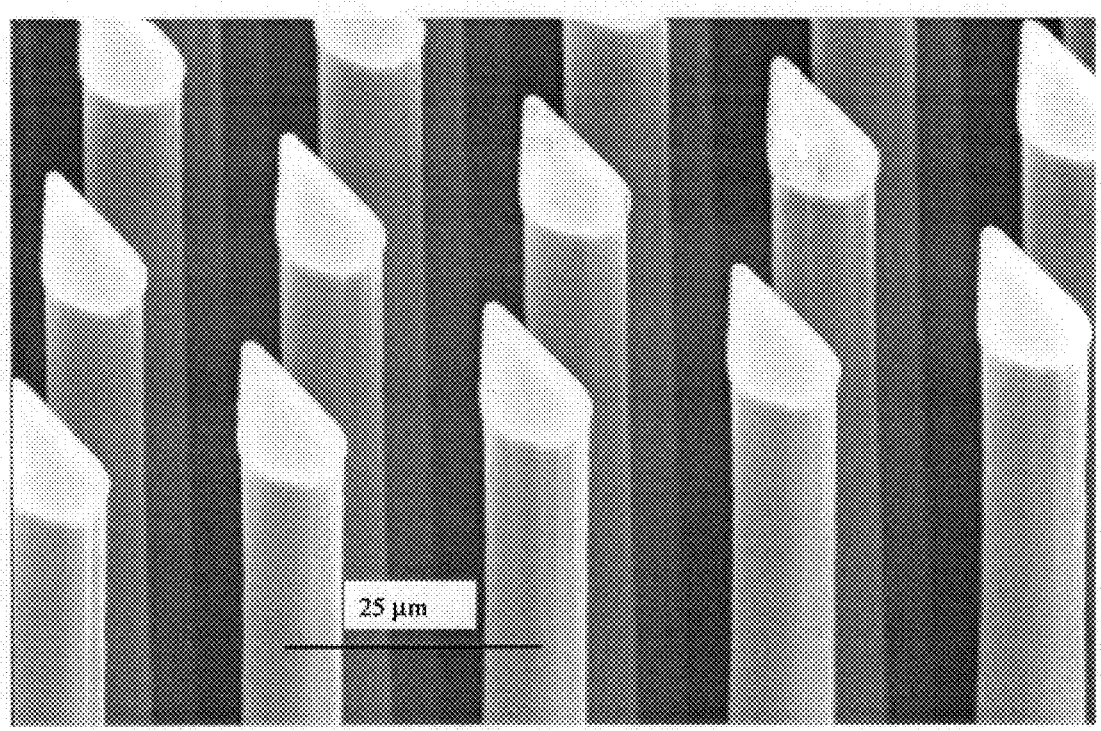
Figure 1D:
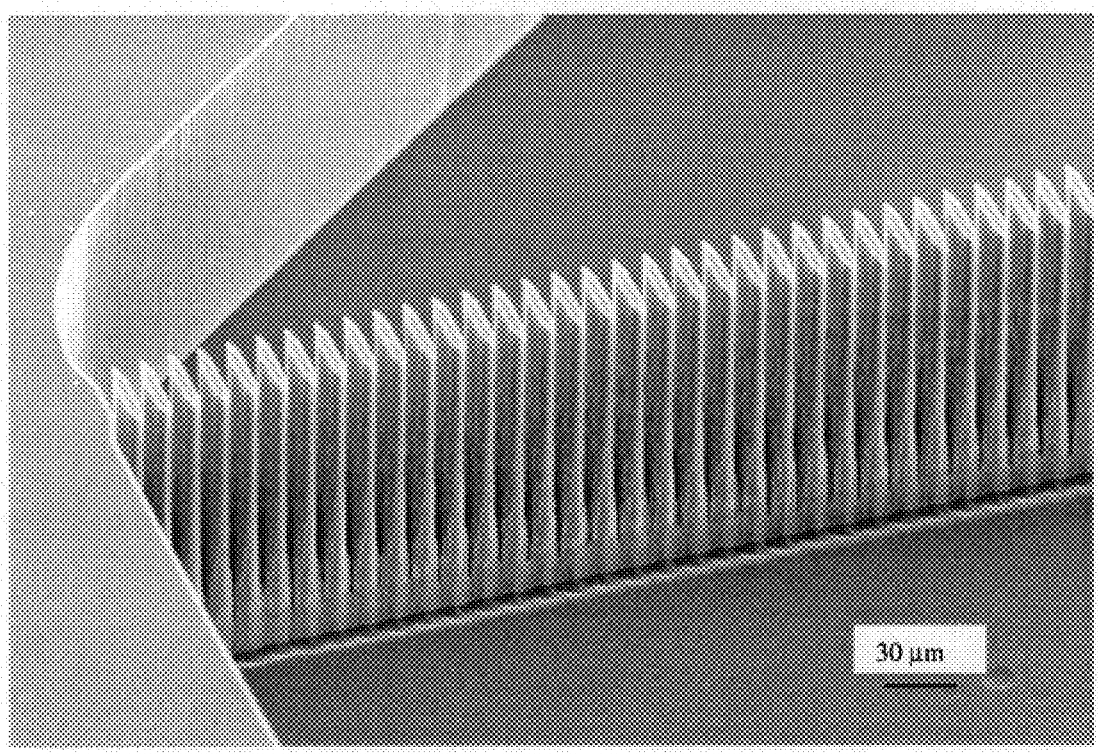
Figure 1E:
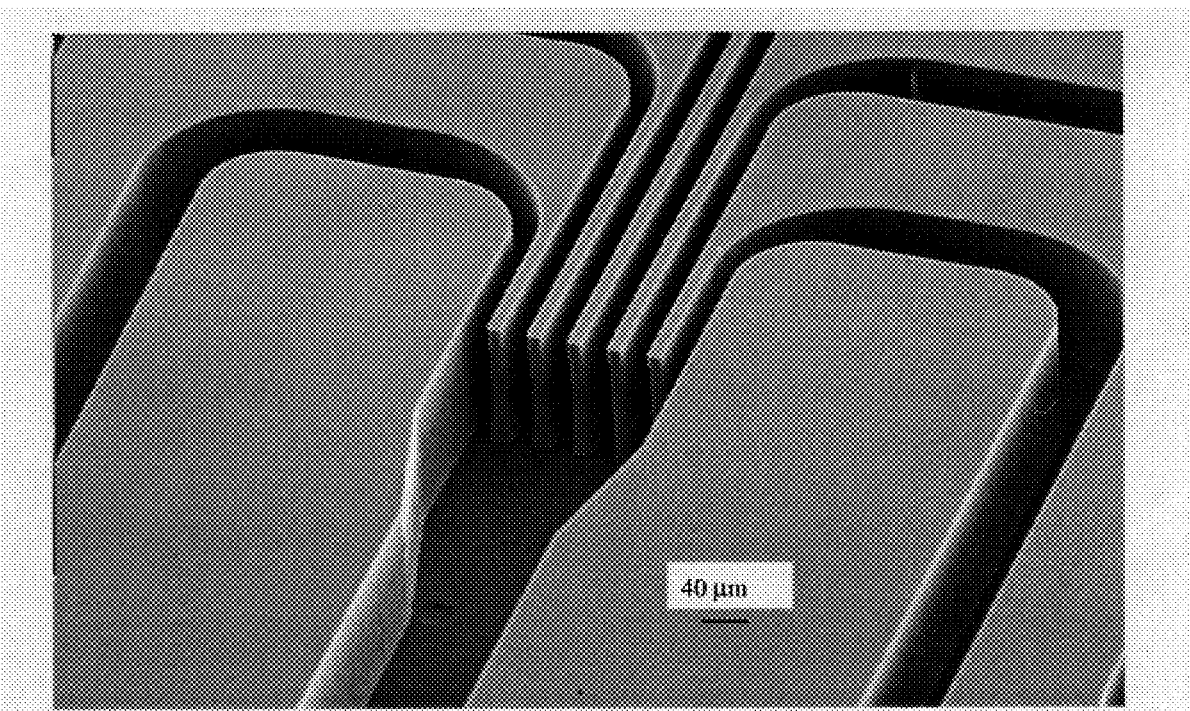
Figure 1F:
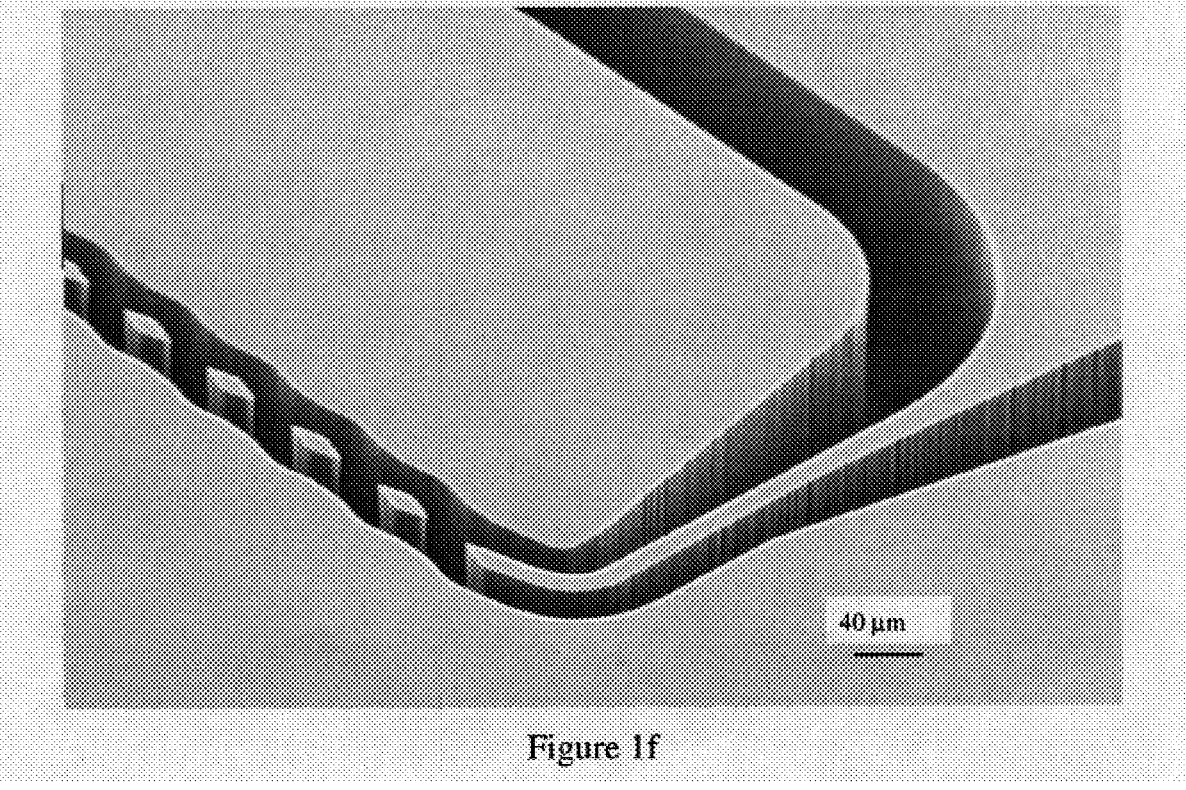
Figure 1G:
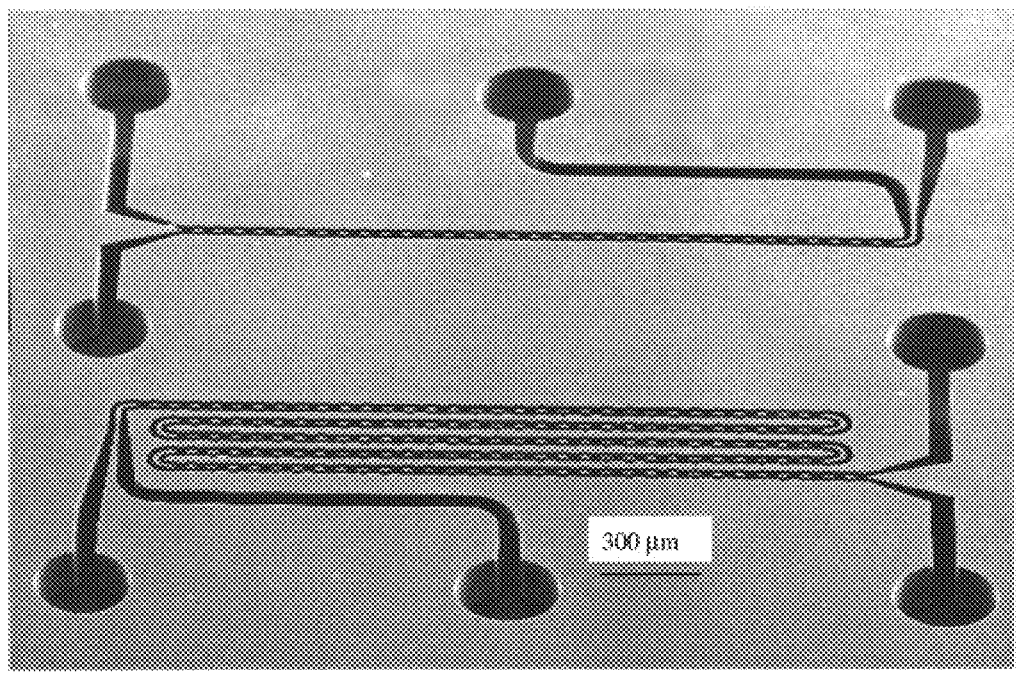
Figure 1H:
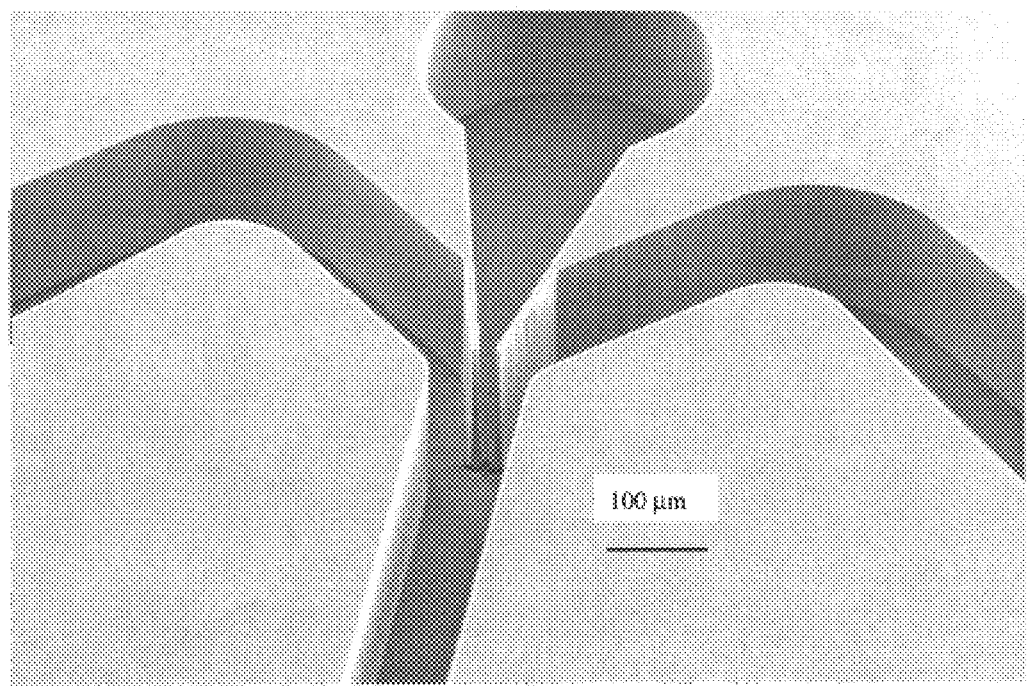
Figure 2:
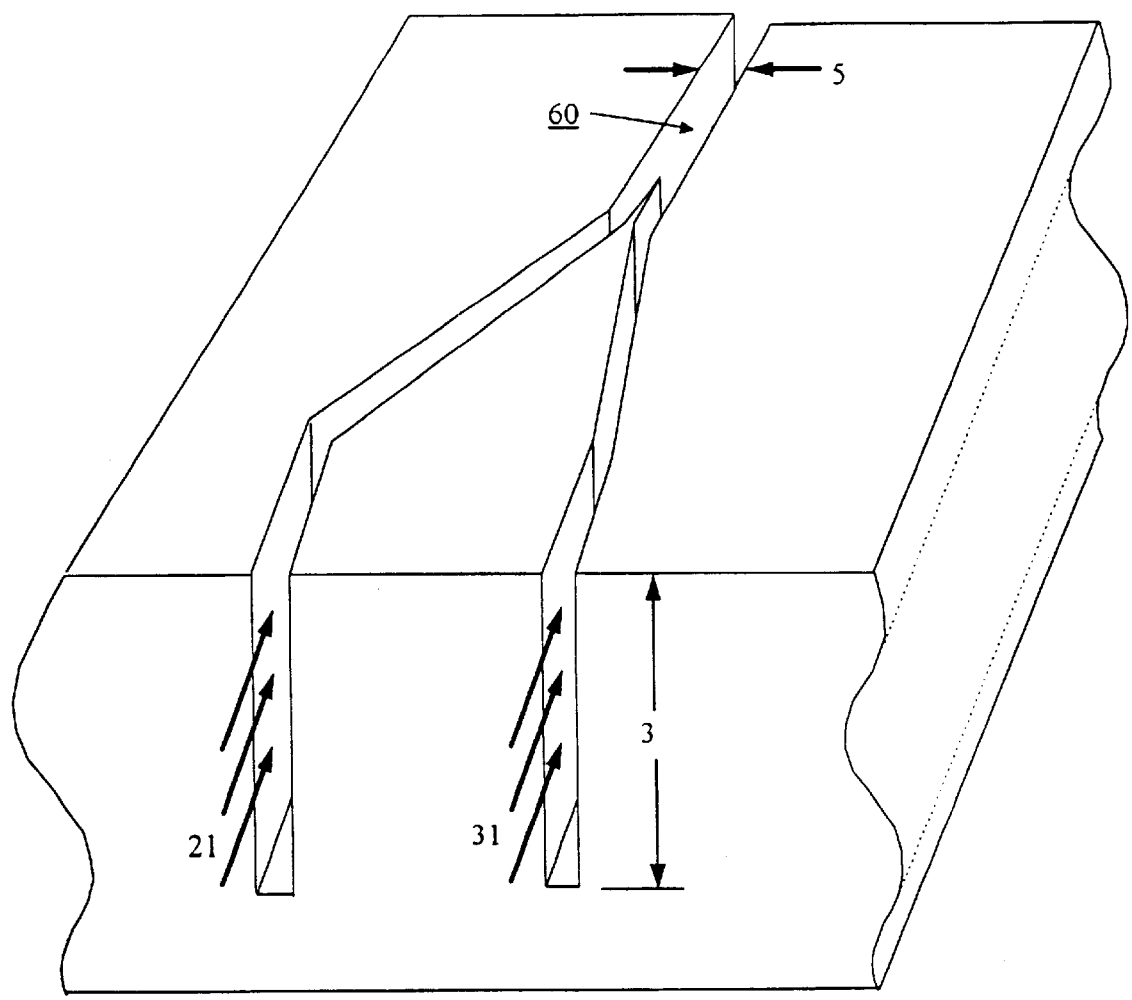
FIG. 2 shows a device of this invention having two deep channels, 21 and 31, converging into one, 60, etched in a silicon matrix using deep reactive ion etching (DRIE). The ratio of the depth 3 to the width 5 is greater than 1:1, providing a surface area ratio of greater than 3:1. Fluids flowing through the separate channels merge to form two thin fluid sheaths flowing side-by-side in the single channel. The channels may be about 10–1000 μm deep. The two thin fluid sheaths provide a large surface area for diffusion mixing of the two fluids.
Figure 3:
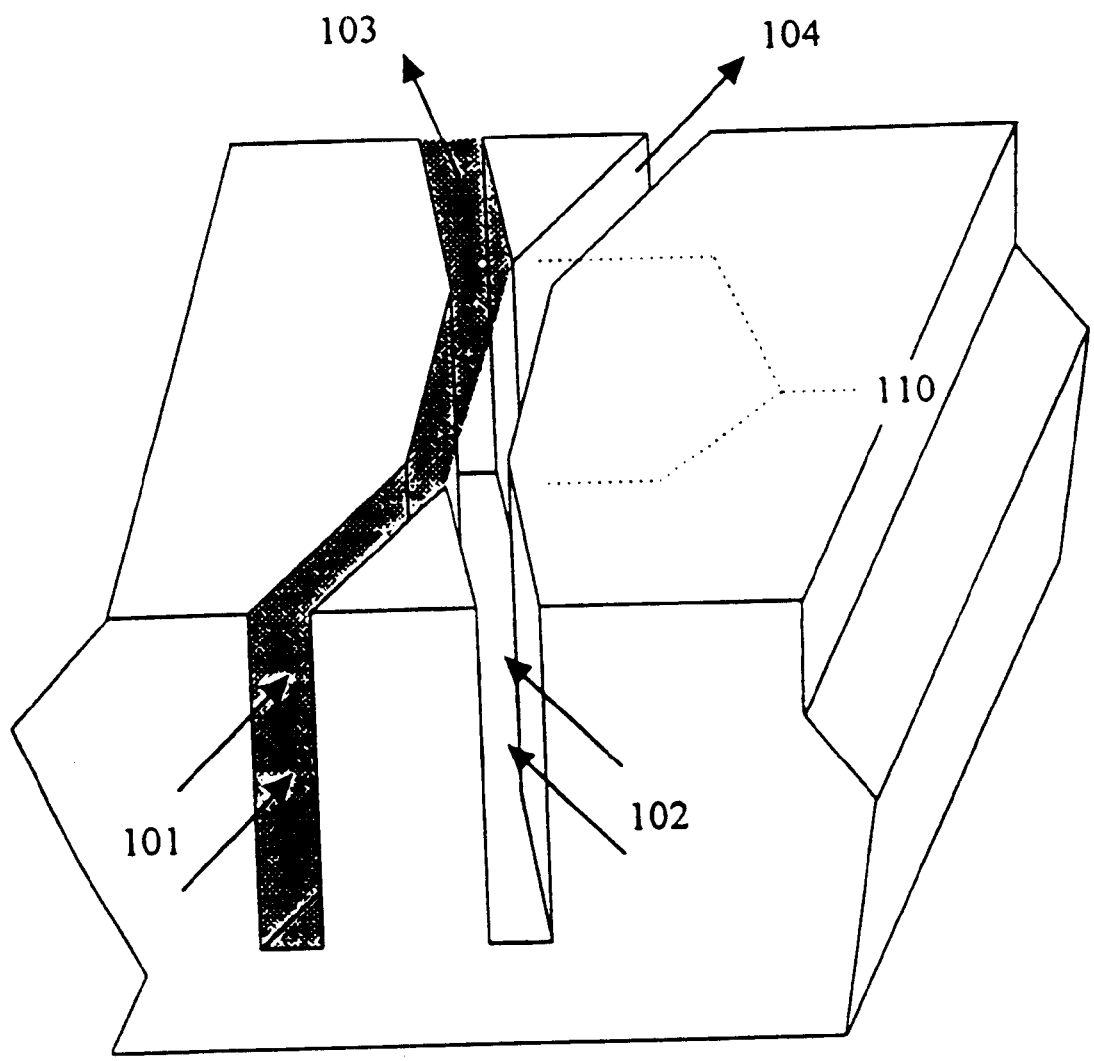
FIG. 3 shows a device of this invention having two high surface area ratio channels 101 and 102 wherein two immiscible fluids (nonpolar and polar solvents) are illustrated in flowing relationship. The channels merge in the contact region 110. Since the fluids are immiscible, they flow alongside each other throughout the region 110, then exit, respectively, into their corresponding channels 103 and 104. During the time the fluids are in the contact region, molecules dissolved in one fluid, but which have partition coefficients favoring the other fluid, will diffuse between the fluids even though the two immiscible fluids do not themselves mix.

As used herein the term "chip" refers to a base substrate approximately 1 to 50 mm on a side and from about 0.2 mm to about 2.0 mm thick. The chamber on a chip thus is a microdevice suitable for the processing of large or small fluid volumes.

As used herein, the term "fluid" includes both gases and liquids, preferably the latter. The fluid may be an aqueous solution or suspension containing particles (e.g., cells, microorganisms, ions, small and large molecules, such as proteins and nucleic acids, etc.) In a particular use, the fluid may be a bodily fluid, such as blood.

As used herein, the term "internal surface area" refers to the total surface area of the interior of the chamber including the surface area of any internal structures, such as microcolumns. In its simplest embodiment, the device of the invention comprises a single channel, so that the "internal surface area" is the summation of the surface areas of the two side walls and the bottom. In this embodiment, the depth of the channel is at least as great as its width to ensure a minimally high surface area ratio.

As used herein, the term "facial surface area" refers to the area on the face or surface of the chip which has been removed to create the internal structure. In the example of the single channel, the "facial surface area" is that of the top of the channel.

As used herein the term "substantially greater" as applied to the ratio of the internal area to the facial area means greater than about 3:1, preferably greater than about 5:1, more preferably greater than about 10:1, and most preferably greater than about 20:1.

The devices of this invention are useful for the high efficiency extraction of cellular components, including macromolecules such as nucleic acids and proteins, from fluid samples and also for providing a highly concentrated eluate of a target of interest. The devices may also be used to perform chemical and biochemical extractions and reactions by introducing various reagents into selected devices and allowing interactions to occur at selected sites. The devices may also be used for heating and cooling of fluid samples. In combination, an array of chambered chips in functional connection may serve to perform any chemical or physical manipulation on a fluid sample. A chamber may be used as a mold for making an impression which in turn may be used to prepare other chambers by casting.

This invention addresses certain aspects of controlling, moving, or otherwise manipulating fluids on a microscale. Microfluidic systems that may be useful for fully automated biochemical analysis require that specific functionalities such as volume measuring, fluid mixing, heating, liquid phase separation, and others, be incorporated into microfluidic circuits. They must be designed to overcome microscale effects, such as low Reynolds numbers, that make conventional macroscopic design approaches ineffective.

Mixing of fluids is a common and critical event in most biochemical analytical protocols. On a conventional macroscale, there are various effective means, including pipettes, vortexing devices, or aspirating/dispensing robotics, to effect mixing of two or more fluids. However, it is well known that mixing of fluids in microfluidic systems is difficult. The problem stems from the fact that the Reynolds numbers are typically so small (less than 100) in most microfluidic systems, that the flows are virtually always laminar. Reynolds number is ([density*velocity*channel-width]/viscosity); in microfluidic systems, the channel width is so small that the Reynolds number is small. In macroscopic systems, Reynolds numbers must be above about 2300 before turbulence begins. Since fluid flow is virtually never turbulent in microfluidic systems, mixing occurs almost entirely by diffusion. Mixing by diffusion can be very slow. One example is that of a 300 $\mu$m deep by 600 $\mu$m wide "zigzagging" channel, which fully mixed only after a flow length of 100 mm.

Various schemes have been proposed to overcome this problem. In the device of Branebjerg a unique micromachined geometry two totally overlapping flows are merged. Because of the two thin ribbons of fluid, the characteristic diffusion length for mixing is now 15 $\mu$m instead of 150 $\mu$m, and diffusion mixing now occurs much more rapidly. In this approach, however, only two channels can be brought together and the total interfacial surface area is limited to the width and length of the channels in the mixing region. To effect mixing under conditions of fast flow-rates, a significant increase in the width of both the individual channels, or an increase in the length of the mixing region, or both, is required. In these cases, the total micromachined device area and cost will be increased.

Besides mixing, other techniques are required in biochemical analysis. For example, one well-accepted technique for extracting proteins and other hydrophobic chemicals from aqueous solutions containing biological compounds is liquid phase separation. Proteins, normally present in high concentration in aqueous biological solutions such as serum, plasma, and tissue homogenates, are structurally composed of both hydrophobic and hydrophilic domains which together determine their secondary and tertiary structure as a function of the solvent in which they are dissolved. Through the hydrophobic domains are usually much larger than the hydrophilic domains, stable structures are achieved in polar solvents when the hydrophobic domains self-associate in the core of the globular structure and the hydrophilic are exposed to the solvent. This satisfies the difference in Gibbs free energy states between folded and unfolded structures as a function of the solvent properties. However, conditions can be produced in the aqueous phase such that in most cases, limited only by extremes of salt concentration and pH or presence of denaturants or detergents, a lower Gibbs free energy state for the protein can be achieved in non-polar solvents, such as alcohols, various alkanes, and chloroform.

The preferential partitioning, migration or diffusion of proteins from polar to non-polar solvents can be exploited to extract proteins from polar-based biological samples. When a non-polar liquid, for example chloroform, is added to a water-based solution, the fluids will not mix, but will remain in two immiscible phases. The less dense non-polar phase will rise to and remain as a separate layer on top of the polar phase. A small number of proteins in the polar phase can undergo a change in tertiary structure and move across the boundary between the two phases because they favor the lower energy state associated with being dissolved in the non-polar phase. Over a very long period of time, the polar phase becomes depleted of proteins. If the immiscible fluids are vigorously agitated, the solutions will form an emulsion. In such an emulsion, the non-polar phase will form into a very large number of small droplets, surrounded by and evenly distributed throughout the polar phase, for example. This effectively dramatically increases the surface area between the two phases for the interaction of the proteins with the non-polar phase and their diffusion into the non-polar phase. The rate of movement of proteins into the non-polar phase can also be enhanced by varying the conditions in the polar phase which decreases their structural stability in the polar phase. The presence of high salt concentration, detergents, phenol, and/or chaotropes can decrease the stability of the folded state of proteins in the polar phase. After the emulsion is allowed to stand still for some time without agitation, or with assistance by increased relative centrifugal force (if there is a density difference between the two phases), the two phases will eventually separate again, with the non-polar phase forming a layer over the top of the polar phase. Now, the non-polar phase is highly concentrated with proteins and the polar phase is depleted of proteins. If the original protein concentration is very high, residual proteins may still be present in the polar phase due to back diffusion, and fresh non-polar solvent must be added and the separation repeated. Similar phase separation methods have been used to separate proteins from water-based biological solutions for many years.

The invention disclosed herein provides microdevices suitable for generating very large microfluidic interfaces useful for effecting fast, efficient mixing of fluids or for creating an artificial emulsion that provides a means for performing the same protein-extraction function as the traditional agitation-based liquid phase separation methods.

For the purpose of generating structures capable of efficient mixing of fluids, new processing technologies have become available for creating micromachined microfluidic channels that make complex types of fluidic geometries, such as the Branebjerg geometry, unnecessary. The process known as "Deep Reactive Ion Etching" (DRIE) enables the design of channels which are surprisingly very deep, yet narrow. With this process the Branebjerg "thin ribbon, fast diffusion mixing geometry" can be realized simply by causing two fluids to flow in deep, vertical channels and merging them together in a simple way, thereby creating two thin vertical fluid sheaths, which will mix by diffusion over a much shorter distance than in traditional types of channels.

Figure 4:
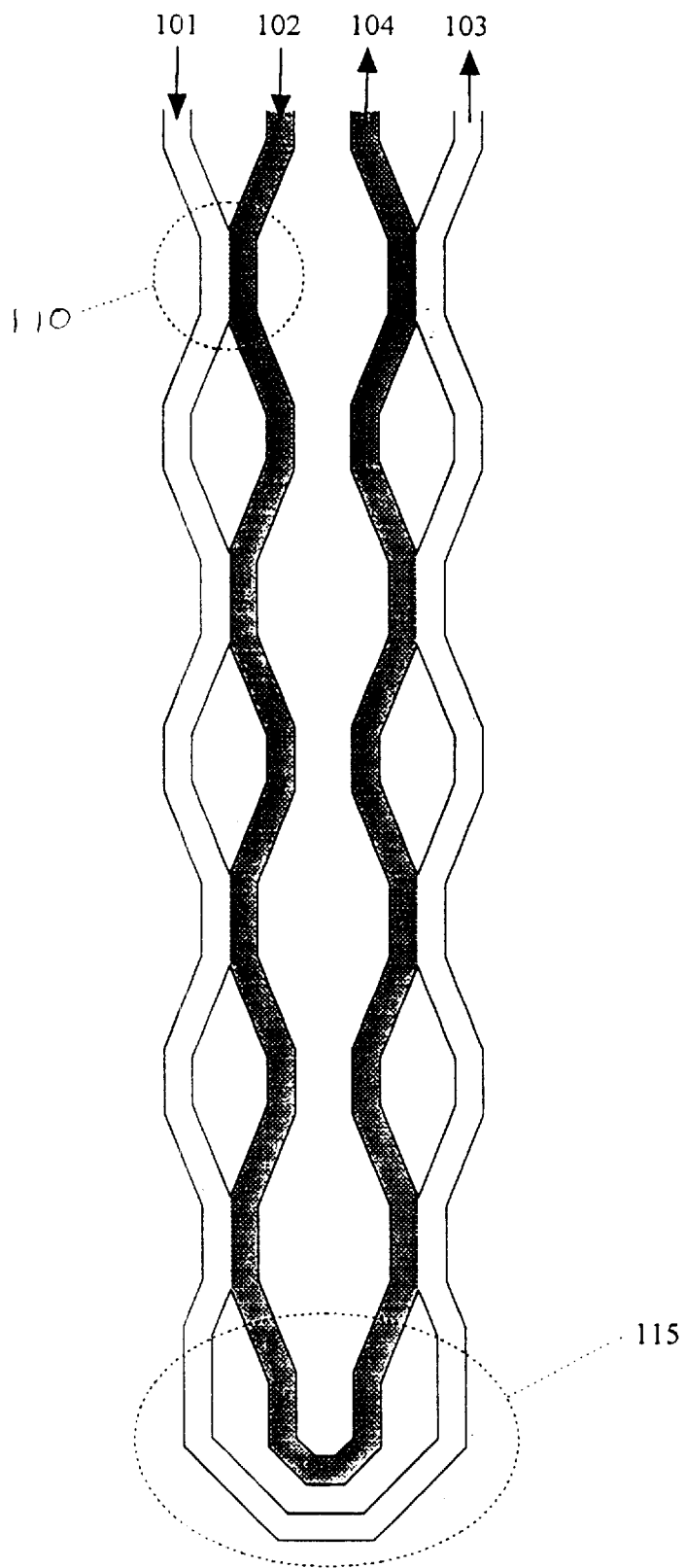
FIG. 4 illustrates a device of this invention having a network of channels 101, 102, 103, and 104, which create multiple interdiffusion regions 110, increasing the fluid contact time. Increased contact time increases particle diffusion. The region 115 shows the fluid flow making a 180 degree turn to increase the total path length on a single chip.

These types of DRIE devices are much easier to produce than the complex Branebjerg geometry and are just as effective for the fast mixing of fluids on a microscale. Additionally, further increases in the total interfacial surface area can be achieved by splitting each fluid input stream into a large plurality of small microchannels which can then be interleaved with a similar number of microchannels from the second fluid or third or more fluids. This approach is impossible with the Branebjerg geometry, and the total effective interfacial surface area is increased by orders of magnitude over that of the Branebjerg geometry within the same total chip area. FIG. 4 shows one such design for the interleaving of multiple microchannels.

Other microchannel geometries that exploit the DRIE process can be designed to support liquid phase separation processes. As exemplified in FIGS. 1–8, fluid channels may be formed on a solid substrate in a wide variety of geometries. The channels have an internal/facial surface area ratio greater than about 3:1. Typical dimensions for the channels will be 10 to 1000 $\mu$m deep and 5 to 50 $\mu$m wide. Although many different methods can be used to form such channels, one typical method is deep reactive ion etching of a silicon, glass, plastic, or metal substrate or layer. The channels are arranged such that two independent channels (each carrying one of the immiscible fluids) intersect and are merged into a single channel. The maximum value for this merged distance will depend on many factors such as the polarity of each of the fluids, the hydrophobicity/hydrophilicity of the inside surfaces of the channels, the degree of immiscibility of the fluids and their surface tensions, the fluid stability of the two thin "sheaths" of fluid flowing side-by-side, their relative flow-rates-and viscosity, and many other factors. Assuming relatively stable fluid "sheaths", turbulent mixing is precluded because of low Reynold's numbers, and since the fluids are also immiscible, they will not mix by diffusion either. After this distance, the merged channel is split into two channels again, allowing the two immiscible fluids to separate again.

During the time and distance over which the two independent streams are merged and in contact at the interface, proteins and other hydrophobic solutes at the interface, will diffuse across the interface into the non-polar fluid stream. When the two streams first make contact, the proteins are uniformly distributed throughout the polar fluid. However, as the fluids traverse the merged channel, the protein concentration in the polar fluid at the interface of the two fluids begins to decrease as proteins move across the interface into the non-polar fluid, forming a depletion zone in the polar fluid at the interface and a concentration gradient across the width of the polar fluid stream. The rate at which the depletion zone is replenished is a function of the concentration gradient formed and of the solute diffusion coefficients, which can vary for different proteins. Since the width of the polar stream is very small, the replenishment rate of the depletion zone will be very fast, so more and more proteins will be absorbed into the non-polar stream as the fluids traverse the diffusion region. After the stream exits the merged channel region, the proteins remaining in the polar stream will equilibrate toward a uniform distribution again; however, the total concentration of proteins will have decreased.

If many such diffusion regions are arranged in series, increased levels of proteins will be removed from the polar stream and will be absorbed by and dissolved into the non-polar stream. It would be straightforward to incorporate very many such diffusion regions into a small microfabricated element, such as a silicon chip. For typical geometries indicated here, at least 50 diffusion regions/mm$^2$ of chip surface area are possible.

Figure 5:
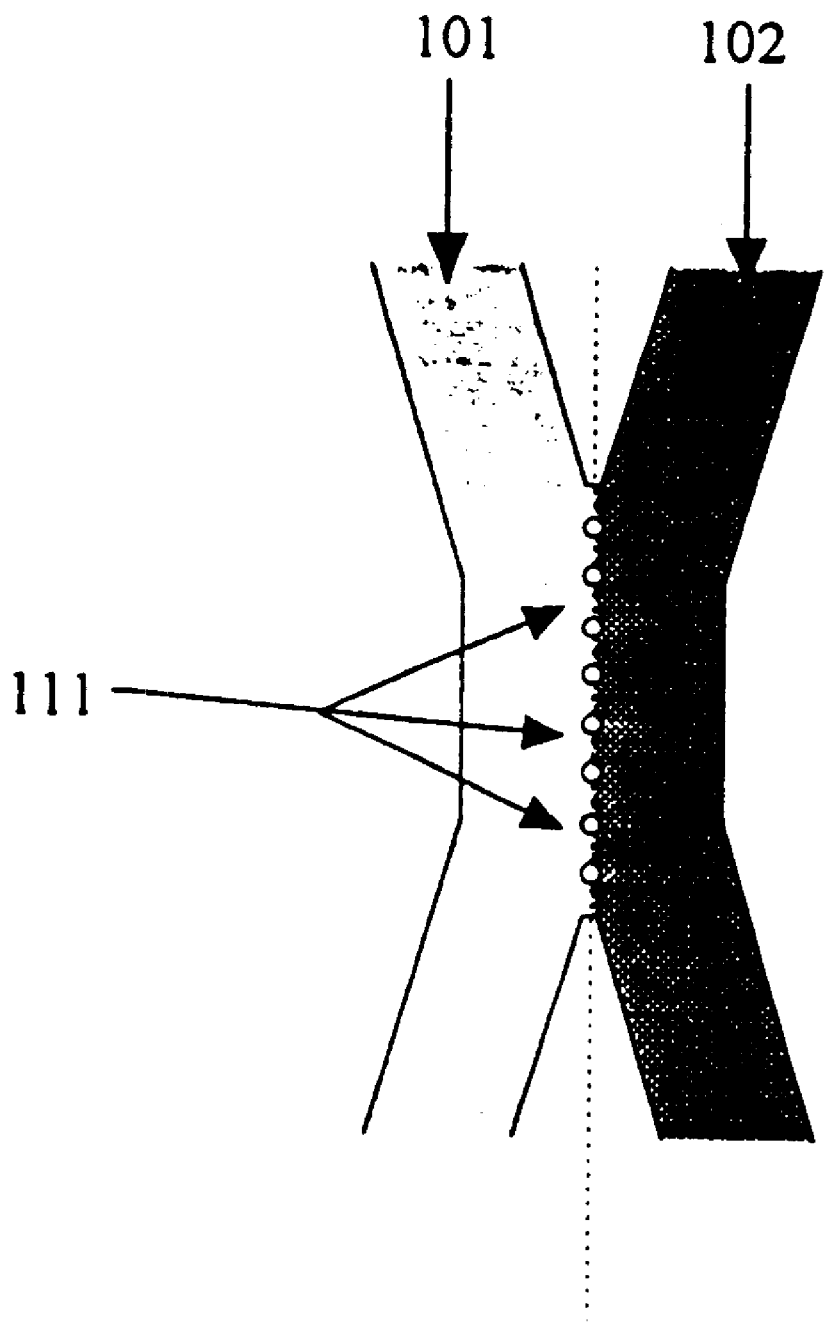
FIG. 5 shows a device of the invention having microcolumns 111 within the diffusion region between channels 101 and 102.
Figure 6:
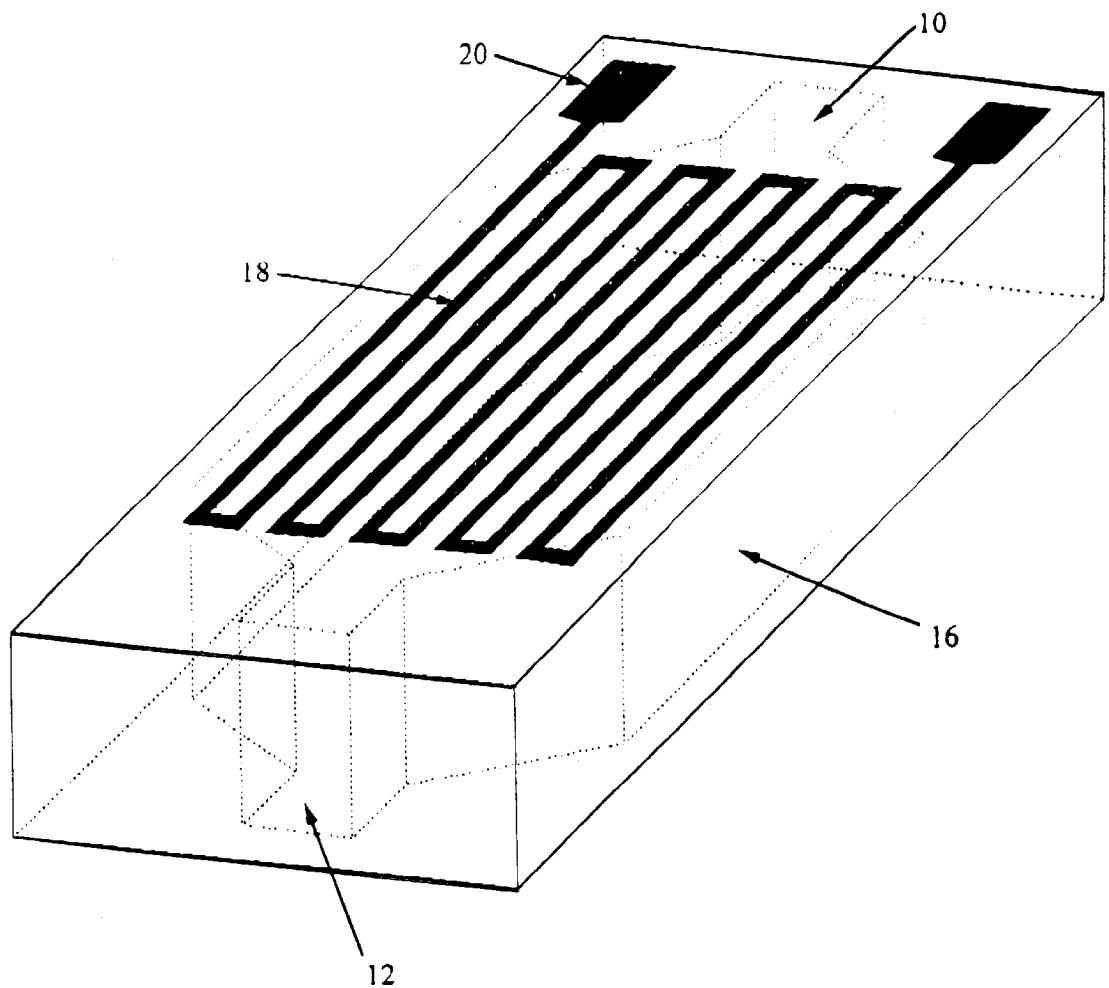
FIG. 6 illustrates a chamber 16 having inlet and outlet ports 10 and 12 and a thin film or diffused resistance heater 18 for with wire bonding pads 20 for external connection.
Figure 7:
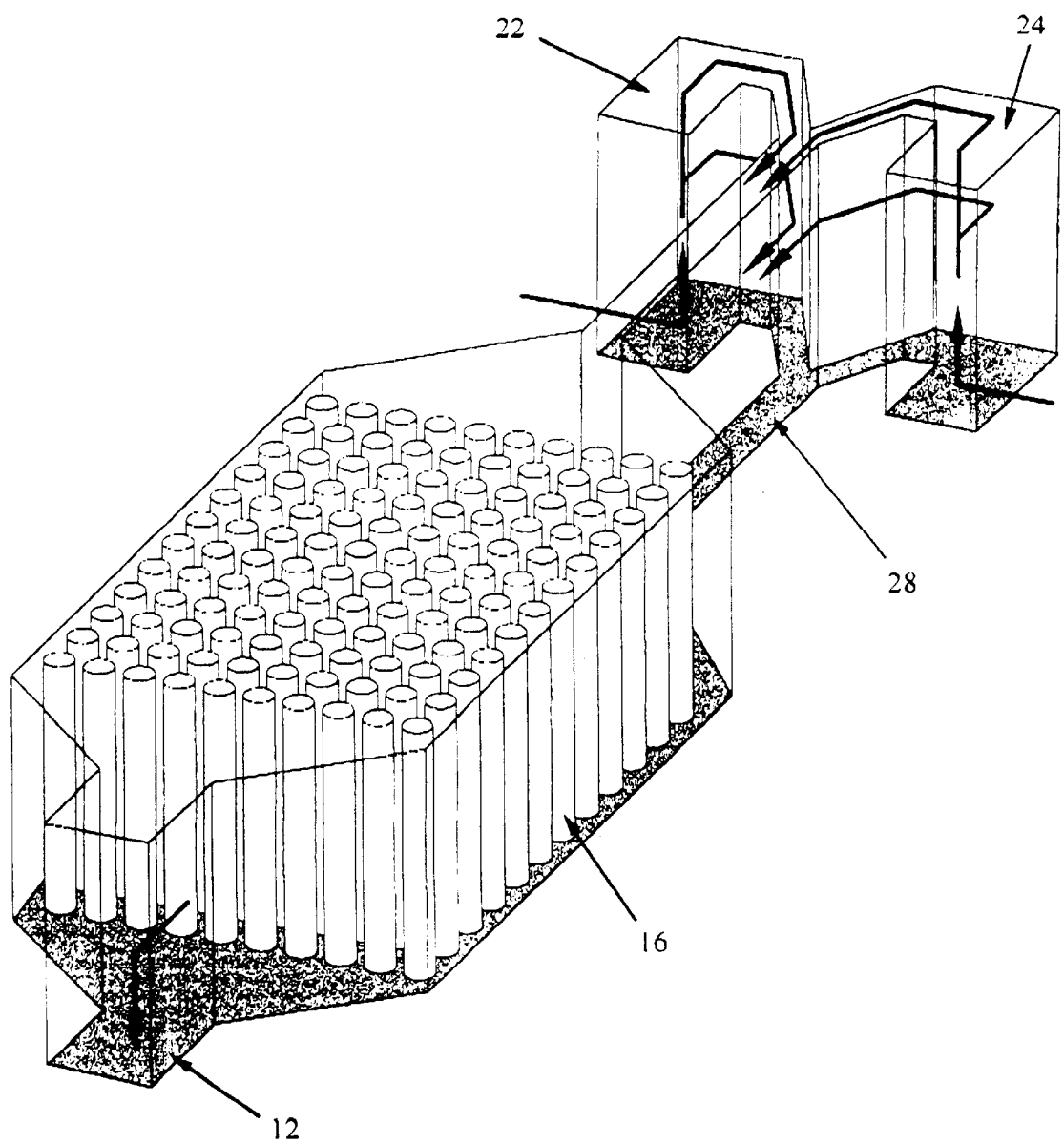
FIG. 7 illustrates two chamber designs on a single chip. Fluid enters input ports 22 and 24 and passes through channeled diffusion mixing region 28 into columnar region 16 having output port 12.

Many variations on this concept are possible. For example, depending on the stability of the fluid streams in contact with each other, it may be possible to have a very long diffusion region, with no equilibration regions. In this case, the fluid flow could be "flat" on the surface of the element. On the other hand, if the stability of the fluid streams is very low, it is possible to provide additional very small "pillars" along the diffusion interface (like miniature jail bars) to further reduce the tendency of the fluids to mix or the streams to become unstable. This is shown in FIG. 5.

A great degree of flexibility can be achieved by the ability to modify the surfaces of the channels to increase the stability of the fluid streams and prevent physical mixing. For example, if the channel surfaces in the regions intended to carry the non-polar fluid are designed to be hydrophobic, then the tendency of a polar fluid to inadvertently flow into the non-polar region, for example, as a result of accumulative small differences in flow-rate and viscosity, is greatly reduced.

The claimed device may be fabricated using a variety of techniques, including photolithography and/or micromachining. The device consists of an enclosed chamber on a chip, optionally containing a three dimensional array of reaction/extraction structures; the size and shape of the structures optimized to be consistent with the objective of efficient interact ion with target moieties in the fluid sample. In general, a device with a large number of internal microcolumns may be fabricated using microlithography techniques. Fabrication is carried out on silicon or other suitable substrate materials, such as glass, silicon dioxide, plastics, or ceramics.

Figure 8:
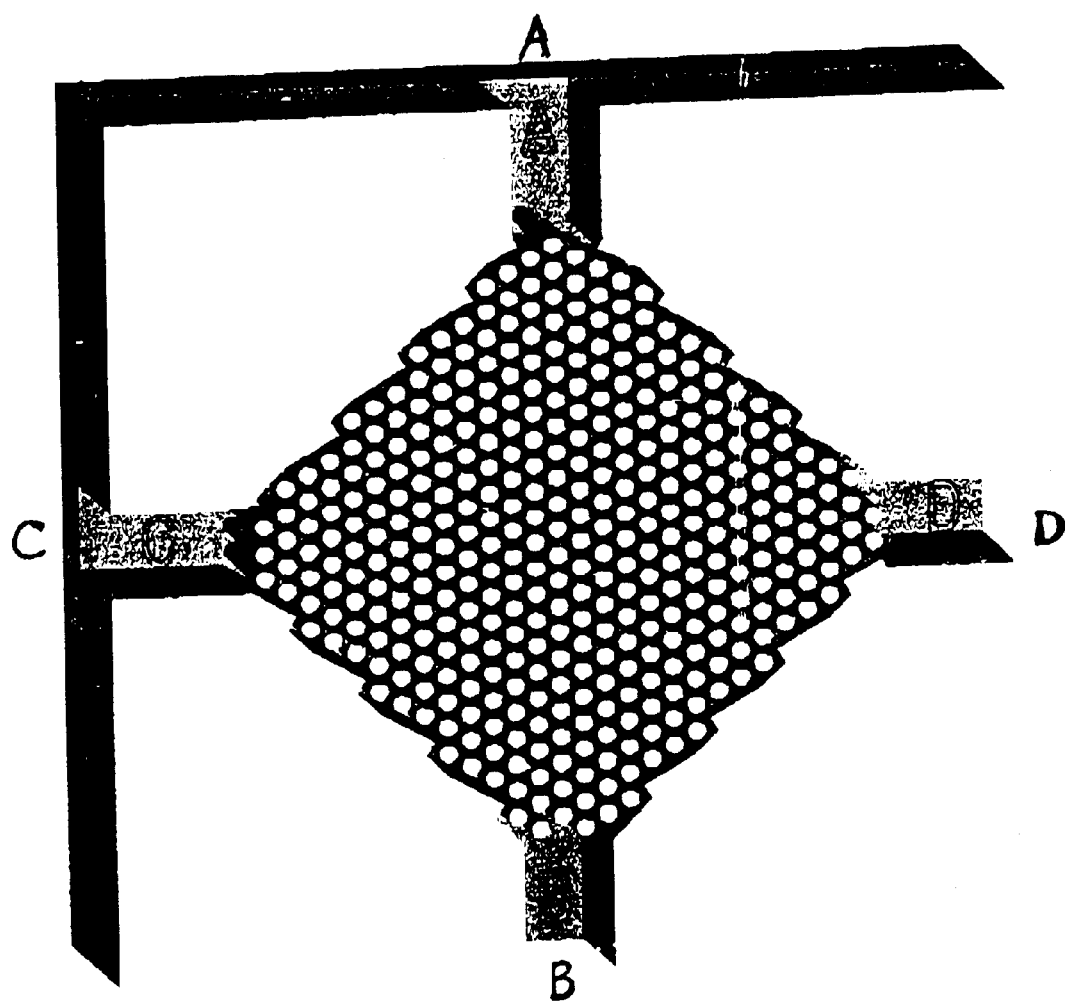
FIG. 8 illustrates a microcolumnar device having four ports.

The devices disclosed herein typically comprise a chamber on a chip having either a network of channels or a densely packed array of high aspect ratio columns etched into silicon using the deep reactive ion etching process. The simplest pattern is a hollowed out chamber of any geometry, which may optionally be wholly or partially filled with a filling material, such as glass beads. Other representative patterns are shown in the Figures. After etching, the silicon surfaces (including the surfaces of the columns) may be coated with an insulator such as silicon dioxide, silicon nitride, or an electrically insulating polymer. The chamber containing the columnar microstructures also includes input and output fluid ports (four are shown in the device of FIG. 8; one is an option for disposable devices). The device may be sealed by bonding a silicon, glass, or other suitable wafer over the etched pattern. The internal structure of a single chip may vary among the many different configurations obtainable as desired.

The microcolumns may be of any shape or size so as to provide a high surface area array. The individual columns are preferably round, square, or rectangular. The height of any individual column may vary and can be of any size, preferably ranging from about 20 to about 1000 microns. It is generally desirable to use high aspect ratio microcolumns, (ratio of height to width and/or diameter), such as 2:1, preferably 10:1, more preferably 20:1. The columns may be uniform in size and shape, or individually eccentric. The columns may, for example, be solid or porous. The columns may be comprised of electrically conductive materials, such as silicon, optionally coated with an insulator, such as, but not limited to, silicon oxide or nitride, or ceramic, of appropriate thickness to create a capacitance structure. In this aspect, the surfaces of the structures are non-conductive.

An exemplary use of the device of the present invention is for the extraction, purification, and concentration of nucleic acids from a complex biological sample. The flow through embodiments will, of course, have more than one port to permit passage of the fluid, as well as having minimal internal dead space. The sample moves through the device by the application of pressure or vacuum or via a potential difference, and the nucleic acids become attached to the reaction/extraction structures by chemical, electrical, or physical absorption or adsorption. Extraction efficiency depends, inter alia, upon the size, shape and composition of the structures, as well as on their number, density, and arrangement in the array, the composition of the buffer or carrier solutions, and reaction and fluid flow rates. A wide range of sample volumes may be processed, from less than ten microliters to many milliliters. During the flow of sample, materials that do not bind to the extraction/reaction structures pass through the device or, if weakly bound, may simply be removed by washing with solvents or detergents, by electronic manipulation such as electrophoresis, or by physical manipulation such as ultrasonic shearing. In this regard, a chamber or series of chambers may be used for chromatography, gas, liquid, ion exchange, and the like, and may optionally be directly attached to other separation and/or detection devices such as infrared , NMR and mass spectrometers.

Further, it has been found that a simple variation of this device, useful even on a macroscopic scale, may be used to selectively manipulate materials, such as particles, cells, viruses, nucleic acids, proteins, etc. in solution or suspension. In essence, a thin insulator with an underlying conductor serves as the manipulation means. The insulator thickness may be from about 0.01 $\mu$m to about 10 $\mu$m thick, and may be any suitable insulator material which is amenable to processing into such thicknesses. The insulator is preferably a silicon compound, including but not limited to silicon carbide, dioxide, and nitride. An AC or DC voltage (0.1 to 100 V) is applied to the conductor. The materials which may be manipulated in a device of this type bear either a permanent charge (e.g. ionic compounds) or may be induced to bear a charge for a period of time sufficient to effect the desired manipulation (e.g. polar or polarizable compounds). Polyanions (e.g. DNA and RNA) and polycations (e.g. many proteins) are thus suitable materials. The materials may be selectively attracted to the insulator surface from which they may subsequently be released either by reversing (or removing) the voltage or by other chemical or mechanical means. Alternatively, materials may be repelled or repulsed from the surface by use of an opposed polarity charge. These effects may be achieved in any size and shape device provided that a thin film insulator is used. As such, this aspect of the invention is not restricted to the chambers disclosed herein, but is expected to be of utility in other configurations as well. A preferred embodiment is the use of such a modification in the chambers described in this specification.

In one embodiment, vertical columns are fabricated from a single substrate so that they are electronically and physically uniform. Prior to introducing the sample into the device, a voltage can be applied to the device to create a surface charge of controlled density uniformly covering the surfaces of all of the extraction/reaction microstructures. Transport of cellular components through the device is accomplished by positive flow of the sample through the enclosure. The dense packing of the columns assures a high probability that target moieties will physically come into contact with the columns. The composition of the buffer/carrier solutions may be modified to control the charge distribution on the surface of the columns, as well as the net charge of the target macromolecules. For example, the depth and density of the charge at the surface of the microstructures is markedly influenced by fluid pH and ionic strengths. Attachment of target moieties may be enhanced, for example, by using ampholines, zwitterions, and large bulk macromolecules codissolved with the target, or by pulsing the polarity of the applied voltage, such as in dielectrophoresis. The latter method may be used to separate weakly bound non-target compounds from more strongly bound target moieties during the flow of the specimen or of wash solutions. An AC voltage may be tuned to a frequency that facilitates the attraction and retention of DNA, but not other molecules, to the structures. After the entire volume of sample has passed through the device, various rinsing solutions may be introduced into the device to effect the removal of loosely bound, undesired material. Changes in pH, salt concentration, or the use of additives, such as detergents or chaotropes, may be used to enhance such removal.

For elution, a small volume of carrier solution is introduced into the device, the voltage polarity reversed, and the nucleic acids released from the reaction sites and allowed to flow out of the device as a highly concentrated bolus. The efficiency of release may be enhanced by using dielectrophoresis, in which an AC frequency is selected which drives the nucleic acids away from the extraction/reaction structures.

The attachment to, or release of, biological analytes from the structures may also be enhanced by providing a means to transmit ultrasonic energy to the device. The structures may be induced to oscillate to increase the frequency of contact between individual molecules and the columns in an extraction process or to cause shearing of the molecules from the structures during the release or elution step.

Additionally, a piezoelectric ceramic disk may be bonded to an exterior surface of the device. Application of an AC voltage to the disk will induce flexing and hence flex the array of microstructures. At resonance, the movement of the structures is maximized. The integration of a miniature ultrasonic horn into the device may also achieve this goal.

Resistive heater elements may also be incorporated into the devices by depositing or diffusing thin-film metal or polysilicon on selected surfaces. Controlled heating provides additional functional capabilities, such as thermal denaturation of proteins and nucleic acids and lysis of cells, as well as high efficiency thermal cycling for polymerase and ligase chain reactions. Cooling features may also be exploited in high surface area structures, modified, for example with external cooling fins.

In another embodiment, a separate set of reaction structures comprised of conducting materials may be included in the device. These can serve as electrodes to effect electrophoretic pulses to increase the probability of the macromolecules encountering the non-conducting, but charged, reaction sites. They can also be used to facilitate the removal of bound target molecules from the array of non-conducting reaction structures. The latter may be accomplished with or without the concomitant reversal of the voltage polarity of the non-conducting capacitance electrodes and with or without chemically-mediated desorption. Adjacent, individually controllable electrodes may be used to induce high fields for electroporation, for example to lyse cells or spores.

In another aspect of the invention, ligand binding methods can be adapted for use with the structures of the device. Ligand binding entities, such as nucleic acids and proteins, may be attached actively or passively to the surface of the structures, to form a specific analyte-capturing surface. ligand coupling chemistries, such as silane-based chemistries, may be used. Bifunctional linkers, with one functionality binding to the internal surface and the other to a target in the test sample may be employed. A sample containing the test analyte may then be passed through the device; analyte binds to the ligand covered surface. After subsequent washing with one or more wash solutions, the ligand-analyte complexes can be eluted as described above. Alternatively, a secondary anti-analyte molecule conjugated to a reporter molecule may be passed through-the device, so that the conjugate is captured by the analyte. This complex may also be eluted.

The devices of this invention are also useful for combinatorial synthesis of biopolymers such as oligonucleotides and polypeptides. Combinatorial synthesis allows very large numbers of sequences to be synthesized in a device by transporting, concentrating, and reacting monomers, coupling and deblocking reagents, and catalysts at separately addressable reaction/extraction microstructures. This use exploits the ability of the device to insulate selected microstructures from each other and from nearby reagents.

One method of operating a device is described below.

The sample to be manipulated is forced to flow into port A of FIG. 8. The sample may consist of any fluid biological material including nucleic acids (DNA and RNA), proteins, lipids, cellular debris, and other materials. During this phase, a positive voltage is applied to the silicon substrate (which simultaneously applies a voltage to the inner core of all the silicon columns). As the sample flows through the chamber from port A to port B, the positively charged columns attract, capture, and hold any nucleic acids which pass by. As increased amounts of sample flow through the chamber, more DNA or RNA is accumulated on the positively biased surfaces of the structure.

After a sufficient quantity of sample has flowed through the chamber, ports A and B are closed. A buffer or carrier solution is then forced to flow from port C to port D. Simultaneously, the voltage applied to the silicon is reversed from positive (which holds the DNA or RNA) to negative, releasing the DNA or RNA attached to the coated silicon surfaces into the carrier solution flowing from port C to port D, thereby transporting them out of port D into another region of the fluidic analysis system for further analysis or other manipulation. Local changes in solvent polarity or pH will augment the reaction.

Alternatively, the device can be used to concentrate DNA or RNA. After a sufficient quantity of sample has flowed through the positively charged microstructure, the subsequent carrier solution is passed through the structure. The flow is then stopped and the voltage bias reversed. After a short time, the carrier flow is resumed. The released DNA or RNA will travel out of the microstructure as a concentrated bolus. This mode of operation may only require one inlet port and one outlet port, rather than four.

This basic mode of operation can be modified in many ways. For example, various reagents, buffers, or washes may be passed from A to B to C to D while maintaining the positive voltage on the silicon, thereby flushing away any interfering organic material. These various washes, optionally at different pH levels, may be combined with varying voltage levels to maximize the removal of certain materials and minimize the removal of other materials. The washes may be sequenced, first at one specific voltage level and one specific pH, followed by a different specific voltage level and a different specific pH. The voltage may be ramped up or down during the wash to remove different types of organic material in different sequences.

The preparation of certain devices of this invention is described in the following Examples, which are presented for illustrative purposes only and should not be construed so as to limit the invention disclosed and claimed herein.

EXAMPLE 1

High surface area ratio structures may be realized by standard silicon wafer processing and deep reactive ion etching (DRIE) as follows. A four inch, (100) p-type, 1–10 Ohm-cm, double side polished silicon wafer is used as starting material. The wafer thickness is in the range of 350 to 600 μm, depending on the desired structure. The wafer is spun with positive photoresist (available from, e.g. Shipley) to obtain a photoresist thickness sufficient to mask the deep RIE process. This thickness depends on the final desired depth of etch. The ratio of silicon etch rate to photoresist erosion rate is typically greater than 50:1. To etch structures that are 200 μm deep, 4 μm of photoresist is sufficient. The photoresist is softbaked at 90° C. for 30 minutes, then exposed with the desired mask pattern, developed and hardbaked, using processes well known to those skilled in the art of silicon wafer processing.

The patterned wafer is then etched with a DRIE process. A device useful for etching is available commercially (Surface Technology Systems Redwood City, Calif.). The process involves the use of inductively coupled plasma etching and deposition in an alternating fashion, using fluorine based chemistry. Aspect ratios of 20:1 are easily realized. The etch rate is approximately 2 μm/min.

After etching, the photoresist is removed from the wafer, either with oxygen plasma ashing, or wet chemical stripping in sulfuric acid. The wafer is then anodically bonded to a Pyrex glass cover. The glass cover has holes in it to allow the process fluid to enter and exit the structure, the holes being fabricated, e.g. by ultrasonic milling (Bullen Ultrasonics Eaton, Ohio). The bonding process is well known in the art, involving the application of a positive voltage of about 600 VDC to the silicon relative to the glass, while heating the glass/wafer pair to temperatures in the range of 350–500° C.

After bonding the resulting wafer pair may be diced, and the resulting chip is now complete.

EXAMPLE 2

The preceding Example teaches the production of structures with surfaces of bare silicon. To produce structures with insulating surfaces, such as silicon dioxide, a modified process is used.

The starting wafer is processed first through a thermal oxidation step to yield approximately 100 nm of oxide growth, and then coated with 100 nm of silicon nitride using low pressure chemical vapor deposition (LPCVD). The wafer is then processed through the photoresist patterning process described above in Example 1.

Before the DRIE etch, the nitride is etched using plasma etching (e.g. $CF_4$ and $O_2$), and then the oxide is etched using a buffered oxide etch (BOE). The wafer is then DRIE processed to produce the high aspect ratio structures. The photoresist is stripped, and the wafer is cleaned and further oxidized to produce an oxide on the sidewalls of the high aspect ratio structures with a thickness of 500 nm. The wafer is then put through a plasma etch process to remove the nitride on the uppermost surface of the wafer. This process only slightly removes some of the 500 nm oxide. A short BOE etch then removes the 100 nm of oxide from the uppermost surface.

After this step, the uppermost surface is bare silicon and is easily bonded to the Pyrex cover, whereas the high aspect ratio structures have at least 300 nm of oxide remaining. The processing continues as described previously with anodic bonding and final dicing of the wafer.

The non-planar microstructure has many advantages over planar electrode techniques. Most importantly, deep reactive ion etching allows the silicon columns to be etched with diameters of about 10 microns, spacings of about 5 microns, and heights (or etched depths) of about 100 microns. The total exposed silicon reaction surface area is very high, at least 15 times that of the original planar surface area. The small planar chips fabricated with this process are more cost-effective. The fabrication technique is very simple, requiring only one mask level. The geometrical layout of the capture region is easily changed and optimized to increase total surface area for capture, to optimize flow resistance, and/or to create different fluid resistances.

The advantages of the invention for the efficient extraction, concentration and elution of desired materials from complex samples include:

(1) Continuous flow of specimen through an enclosed array of densely packed microstructures of high surface-to-volume ratio assures that specimens containing low concentrations of target can be efficiently processed.

(2) Dense packing increases the probability of capture by the structures assuring that the target can be efficiently extracted and highly concentrated.

(3) Any one of, or a combination of means, such as voltage reversal, electrophoresis, ultrasound, heating, cooling, local changes in pH, or chemical elution may be used to remove unbound materials from the device.

(4) Multiple chips may be linked together on a single base structure to provide a mutiplexed device capable of executing any desired combination of amplification, concentration, extraction, filtration, reaction, and separation operations in any desired sequence. The chips may be physically joined through other chips or through independent fluid channels in the base structure. In one embodiment, the base structure may be a fixed component of a permanent instrument, with associated electronics, and disposable chips may be arranged thereon in the desired pattern to perform the desired functions. The base structure may be designed with built-in alternative pathways for creating a multiplicity of chip patterns.

The following claims particularly point out and distinctly claim that which applicants regard as their invention.

What is claimed is:

1. A device for the manipulation of fluids, the device having at least first and second channels for carrying first and second fluid streams, respectively, wherein the first and second channels converge into a common channel to provide a contact region for the fluid streams, and wherein at least the common channel has a depth greater than its width; whereby the fluids flowing in the first and second channels flow into the common channel to form at least two fluid streams flowing side by side in the common channel.

2. The device of claim 1, further comprising pillars disposed in the common channel to increase the stability of the fluid streams.

3. The device of claim 1, wherein the first and second channels merge into a plurality of common channels to provide a corresponding plurality of contact regions for the fluid streams, and wherein each of the common channels has a depth greater than its width.

4. The device of claim 3, wherein the device includes at least 50 contact regions/mm$^2$.

5. The device of claim 1, wherein the common channel makes at least one 180 degree turn.

6. The device of claim 1, wherein the common channel has a depth greater than 100 um.

7. The device of claim 1, wherein each of the channels has a depth greater than its width.

8. The device of claim 1, wherein each of the channels has a ratio of internal surface area to facial surface area of at least 5 to 1.

9. The device of claim 1, wherein each of the channels has a ratio of internal surface area to facial surface area of at least 10 to 1.

10. The device of claim 1, wherein each of the channels has a ratio of internal surface area to facial surface area of at least 20 to 1.

11. The device of claim 1, wherein the device includes at least three channels converging into the common channel.

12. The device of claim 1, wherein each of the channels has a depth greater than its width.

13. The device of claim 1, wherein the device includes at least six channels converging into the common channel.

14. The device of claim 1, wherein each of the channels has a depth greater than its width.

15. The device of claim 1, further comprising third and fourth channels diverging from the common channel for carrying the first and second fluid streams, respectively, away from the contact region.

16. The device of claim 1, wherein the surfaces of the common channel are hydrophobic.

17. A method for transferring particles between at least two fluids, the method comprising the steps of:
  a) providing a device having at least first and second channels for carrying first and second fluid streams, respectively, wherein the first and second channels converge into a common channel to provide a contact region for the fluid streams, and wherein at least the common channel has a depth greater than its width; and
  b) forcing first and second fluids to flow through the first and second channels, respectively, and into the common channel so that the two fluid streams flow side by side in the common channel.

18. The method of claim 17, further comprising the step of forcing the first and second fluids to flow through a plurality of common channels to form at least two fluid streams flowing side by side in each of the common channels, wherein each of the common channels has a depth greater than its width.

19. The method of claim 17, wherein each of the channels has a depth greater than its width.

20. The method of claim 17, wherein the common channel has a depth greater than 100 $\mu$m.

21. The method of claim 17, wherein the device further comprises third and fourth channels diverging from the common channel for carrying the first and second fluid streams, respectively, away from the contact region, and wherein the method further comprises the step of forcing the first and second fluid streams to flow into the third and fourth channels, respectively.

22. The method of claim 21, wherein each of the channels has a depth greater than its width.

\* \* \* \* \*

UNITED STATES PATENT AND TRADEMARK OFFICE
CERTIFICATE OF CORRECTION

PATENT NO. : 6,368,871 B1 Page 1 of 1
DATED : April 9, 2002
INVENTOR(S) : Christel, Lee Allan; Kovacs, Gregory T.A.; McMillan, William A.;
Northrup, M. Allen; Petersen, Kurt E. and Pourahmadi, Farzad It is certified that error appears in the above-identified patent and that said Letters Patent is hereby corrected as shown below:

Column 14,
Line 14, replace "100☐m" with -- 100 μm --.

Signed and Sealed this

Thirtieth Day of July, 2002

*Attest:*

JAMES E. ROGAN
*Attesting Officer*     *Director of the United States Patent and Trademark Office*